United States Patent [19]

Ohtani et al.

[11] Patent Number: 4,587,543

[45] Date of Patent: May 6, 1986

[54] METHOD AND DEVICE FOR DETECTING METAL IONS

[75] Inventors: Ryoichi Ohtani, Yokohama; Iwao Ohshima, Kawasaki, both of Japan

[73] Assignee: Tokyo Shibaura Denki Kabushiki Kaisha, Kawasaki, Japan

[21] Appl. No.: 382,774

[22] Filed: May 27, 1982

[30] Foreign Application Priority Data

May 29, 1981 [JP] Japan ................................. 56-81967

[51] Int. Cl.$^4$ ............................................ H01L 29/66
[52] U.S. Cl. ..................................... 357/25; 357/23.1; 357/23.14; 357/23.15
[58] Field of Search ..................... 324/71.5, 71.6, 464; 376/250; 357/23 I, 23 MG, 25

[56] References Cited

U.S. PATENT DOCUMENTS

| | | | |
|---|---|---|---|
| 3,438,121 | 4/1969 | Wanlass et al. | 357/23 I |
| 3,586,930 | 6/1971 | Das et al. | 357/23 MG |
| 3,694,673 | 9/1972 | Au | 357/23 MG |
| 4,158,807 | 6/1979 | Senturia | 357/25 |
| 4,218,298 | 8/1980 | Shimada | 357/25 |
| 4,332,170 | 6/1982 | Belval et al. | 376/250 |
| 4,380,168 | 4/1983 | Ibe | 376/250 |
| 4,411,741 | 10/1983 | Janata | 357/25 |

FOREIGN PATENT DOCUMENTS

| | | | |
|---|---|---|---|
| 2947050 | 5/1981 | Fed. Rep. of Germany | 357/25 |
| 56-35037 | 4/1981 | Japan. | |
| 1529743 | 10/1978 | United Kingdom | 357/25 |

OTHER PUBLICATIONS

IEEE Transactions of Biomedical Engineering, Nov. 1974, pp. 485 to 487.
IEEE Transactions of Biomedical Engineering, Sep. 1972, pp. 342 to 351.
Ion-Sensitive Field Effect Transistors, vol. 1, pp. 35-36; 51-53; Pergamon Press Ltd. 1979.
Copy and English Translation of the Official Action.
Sodium-Nak Engineering Handbook, vol. III, Chap. 4, Sec. 6, "Leak Detection", O. J. Foust et al.; 1978.
Journal of Applied Physics, vol. 36, No. 5, "Ion Transport Phenomena in Insulating Films", E. H. Snow et al.; May 1965.

*Primary Examiner*—Martin H. Edlow
*Assistant Examiner*—Jerome Jackson
*Attorney, Agent, or Firm*—Oblon, Fisher, Spivak, McClelland & Maier

[57] ABSTRACT

A device for detecting metal ions in an atmosphere. The device is based on a well known insulated gate-type field-effect transistor (MOSFET). The device includes a metal ion detecting element based on the MOSFET; a means, connected to the metal ion detecting element, for making a current flow through said metal ion detecting element; and a means, connected to the metal ion detecting element, for detecting the change of the strength of the current flowing through the metal ion detecting element, the change being brought by the electric charge of the metal ions which reached the gate oxide film. A metal ion introducing passage for allowing migration of the metal ions to be detected to the gate oxide film is formed in the gate electrode of the metal ion detecting element in the direction of its thickness.

8 Claims, 11 Drawing Figures

W --- EVACUATING PUMP 80 TURNED ON
X --- VALVE 90 OPENED
Y --- Na REACHED CONTAINER 76
Z --- EVACUATING PUMP 80 TURNED OFF

METHOD AND DEVICE FOR DETECTING METAL IONS

BACKGROUND OF THE INVENTION

1. Field of the Invention

The present invention relates to a metal ion detecting device. More specifically, the present invention relates to a metal ion detecting device for detecting leakage of metal ions of sodium or the like which is used, for example, as a coolant for a fast breeder reactor.

2. Description of the Prior Art

Liquid sodium is used as a coolant in a fast breeder. When sodium leaks from the facilities or piping, it is brought into contact with ambient air or moisture to form a corrosive compound. If this leakage is left undetected, the facilities or piping are damaged even when the amount of the leaked sodium is small. This results in a secondary leakage of a larger scale. For this reason, it is necessary to detect leakage at an early stage irrespective of its scale and to take a proper countermeasure.

A conventional device for detecting leaked sodium ions is known which utilizes electrical conductivity of the leaked sodium. The conventional sodium detecting device is arranged in the vicinity of facilities or piping through which sodium flows and includes a trap for collecting the leaked sodium. A pair of electrodes is arranged at the bottom of the trap. The leaked sodium is collected by this trap to electrically conduct the electrodes, so that leakage of sodium is detected. However, this device does not operate until a considerable amount of sodium has leaked. Thus, it is difficult to detect leakage of sodium at an early stage.

Liquid sodium which has leaked to the outside reacts with air to generate white smoke. Therefore, a method for detecting leakage of sodium is known which detects the white smoke with a smoke detector. However, such a smoke detector tends to operate erroneously and has a low sensitivity since it may be operated by dust or other types of smoke than the white smoke.

Sodium which is used as a coolant in a fast breeder generally has induced radioactivity. Another method for detecting leakage of sodium is thus known which incorporates a radiation detector which is arranged near facilities or piping through which sodium flows and which detects leakage of radioactive sodium. However, the secondary coolant of the fast breeder generally has small radioactivity. Therefore, this method fails to detect leakage of sodium as the secondary coolant or sodium which is not radioactive.

SUMMARY OF THE INVENTION

It is, therefore, an object of the present invention to provide a method for detecting metal ions which is capable of detecting metal ions with high precision and which may not operate erroneously.

It is another object of the present invention to provide a device for practicing the method as described above.

The device of the present invention is based on an insulated gate-type field-effect transistor (MOSFET) which is conventionally known. The MOSFET includes a semiconductor substrate, source and drain regions formed in the semiconductor substrate, source and drain electrodes formed on the source and drain regions, respectively, a gate oxide film formed on the surface region of the semiconductor substrate between the source and drain regions, and a gate electrode formed on the gate oxide film. It is well known that the source current or the drain current changes when a voltage applied to the gate electrode is varied. In the metal ion detecting device of the present invention, metal ions to be detected are introduced to the gate oxide film. The gate voltage is then changed by the charge on these metal ions, so that the source current or drain current changes accordingly. The presence of the metal ions can thus be detected through changes in the source current or drain current. In the device of the present invention, in order to facilitate migration of the metal ions to the gate oxide film, a metal ion passage is formed in the gate electrode. With this arrangement, a small amount of metal ions may be detected.

According to the device of the present invention, the presence of metal ions may be detected with high precision as will be described later. The device of the present invention furthermore may not operate erroneously due to the presence of dust or the like. The device of the present invention is suitably adapted for detecting alkali metal ions.

DETAILED DESCRIPTION OF THE PREFERRED EMBODIMENTS

Figure 1:
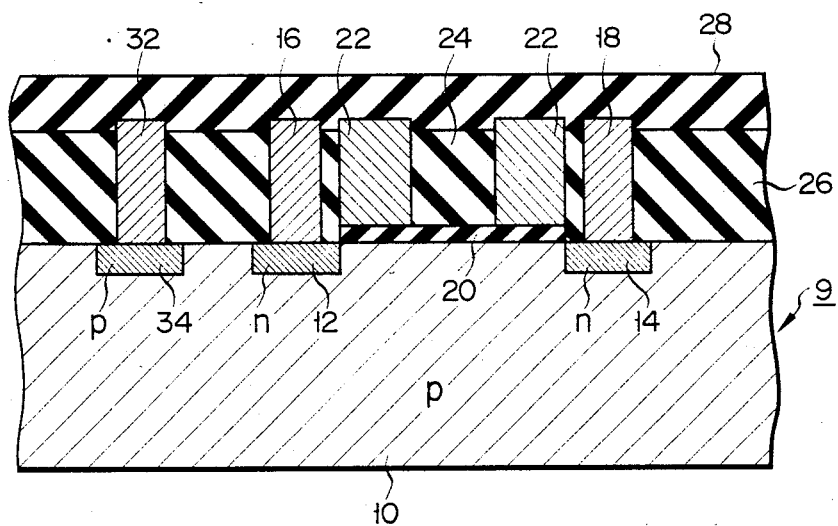
FIG. 1 is a sectional view of the metal detecting element of the metal ions detecting device according to an embodiment of the present invention.

As has been described above, a metal ion detecting device of the present invention is based on an insulated gate-type field-effect transistor (MOSFET). FIG. 1 is a sectional view of a preferable example of a metal ion detecting element 9. An n-type impurity region 12 as the source region and an n-type impurity region 14 as the drain region are formed in a p-type silicon substrate 10. A source electrode 16 of a metal such as aluminum is formed on the source region 12. A drain electrode 18 of a metal such as aluminum is formed on the drain region 14. A gate oxide film 20 of an oxide such as silicon oxide ($SiO_2$) is formed on the surface region of the semiconductor substrate 10 between the source region 12 and the drain region 14. The thickness of the gate oxide film 20 is, for example, 0.1 μm. A gate electrode 22 is formed on the gate oxide film 20. The gate electrode 22 is a conductive layer of a metal such as aluminum and is formed on the gate oxide film 20. A passage 24 for introducing metal ions extends in the gate electrode 22 in the direction of thickness thereof. A field insulating layer 26 of silicon oxide, for example, is formed on the semiconductor substrate. The field insulating layer 26 exists between the source electrode 16 and the gate electrode 22, between the drain electrode 18 and the gate electrode 22, and in the metal ion introducing passage 24. The thickness of the field insulating layer 26 is, for example, 1 μm. A protection layer 28 which prevents gate oxide film 20 from being imbued with metal ions so easily is formed on the field oxide layer 26. The protection layer 28 is made of a material which does not allow migration of metal ions therethrough so easily such as phosphor silicate glass (P.S.G.), $SiN_4$, $Al_2O_3$ or the like. The protection layer 28 has a relatively small thickness. The thickness of the protection layer 28 depends upon its material, the concentration of the metal ions contained in the atmosphere which is not involved in leakage, the required detection sensitivity and so on. The thickness of the protection layer 28 is, for example, 0.3 to 1.2 μm when phosphor silicate glass is used.

Figure 2:
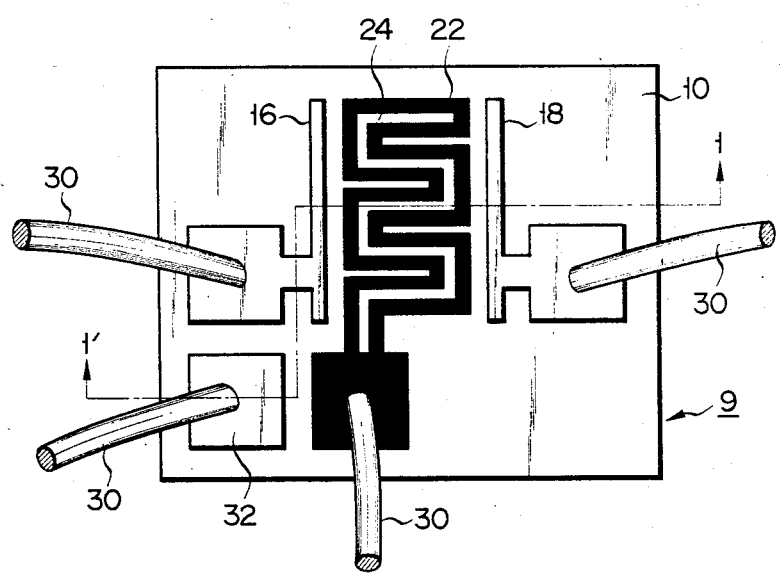
FIG. 2 is a plan view of the element shown in FIG. 1.

FIG. 2 is a plan view of the metal ion detecting device according to the present invention. FIG. 1 described above is a sectional view along the line 1 - 1' in FIG. 2. As may be seen from FIG. 2, gate electrode 22 (painted black in FIG. 2) extend in a meandering manner (bent at right angles). The passage 24 is in the form of a slit which extends along the gate electrode 22. Therefore, the passage 24 also extends in a meandering manner. The gate electrode 22 and the metal ion introducing passage 24 are formed in a meandering manner so as to enlarge the surface area of the opening of the slit-shaped passage 24 while maintaining the distance between the opposing portions of the gate electrode 22. Lead wires 30 are respectively connected to the source electrode 16, the drain electrode 18, and the gate electrode 22. The lead wires 30 are generally made of gold. A subelectrode 32 is also formed on the semiconductor substrate 10. A p-type impurity region 34 (see FIG. 1) is formed below the subelectrode 32. A voltage is applied to the subelectrode 32 so as to maintain the electric potential constant. The subelectrode 32 also serves to make the electric current between the source and drain regions be variable, which widens the range of the detection sensitivity of the device. A lead wire 30 is also connected to the subelectrode 32.

Figure 3:
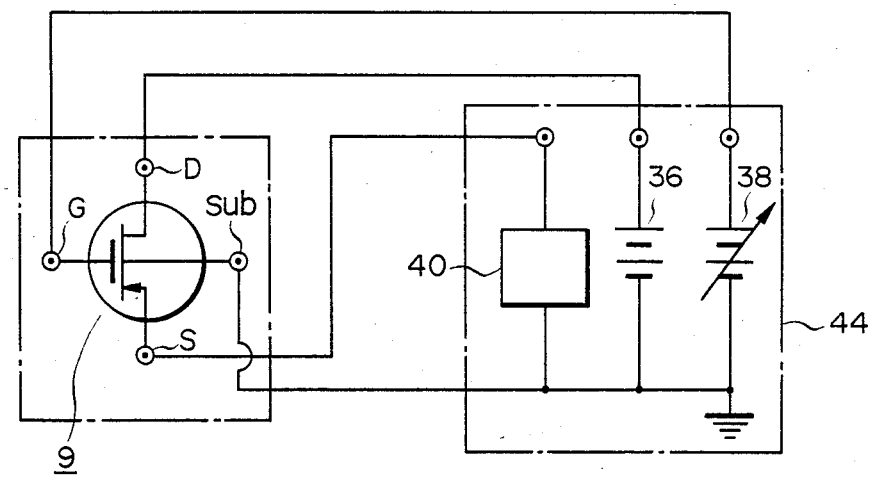
FIG. 3 is a circuit of the device according to an embodiment of the present invention.

A circuit for detecting metal ions with the device as described above is shown in FIG. 3. A voltage of, for example, 200 mV from a constant voltage DC power source 36 is applied across the source electrode and the drain electrode. A positive DC voltage from a variable voltage power source 38 is applied to the gate electrode. By varying the voltage applied to the gate electrode, the sensitivity of the device may be adjusted. A signal processing means 40 is connected to the source electrode. The signal processing means 40 outputs a signal representing the presence of metal ions when the rate of increase of the source current has exceeded a predetermined value. Such a signal processing means is easy to realize for the skilled in the art. For example, an output for informing the presence of metal ions is obtained when the rate of change of the source current exceeds a predetermined value by measuring the source current strength at a prescribed time intervals (for example one minute) and comparing the current strength measured. The subelectrode 32 is grounded.

A description will now be made on the detecting operation of metal ions (description will be made with reference to sodium ions) by the device when the metal ion detecting element 9 of the present invention is placed in an atmosphere containing metal ions. As has been described above, a positive voltage is applied to the gate electrode 22. As is well known, the source region or the n-type impurity region 12 and the drain region or the n-type impurity 14 are then rendered conductive. Since a DC voltage is applied across the source electrode and the drain electrode, a source current (or drain current) flows between the source and drain regions. The source or drain current increases as the positive voltage applied to the gate electrode 22 increases. According to the principle of the present invention, metal ions to be detected are introduced to the gate oxide film 20, the gate voltage is increased by the charge of the metal ions to thereby increase the source current, and the presence of the metal ions is detected through an increase in the source current.

When the metal ion detecting element of the device of the present invention is placed in an atmosphere containing sodium ions, the sodium ions migrate through the protection layer 28. However, the protection layer 28 is made of a material which does not allow easy migration of sodium ions such as phosphor silicate glass. If the sodium concentration in the atmosphere is low, sodium ions do not substantially pass through the protection layer 28. However, the protection layer 28 has a relatively small thickness as described above. Therefore, when the sodium ion concentration in the atmosphere is high, sodium ions can pass through the protection layer 28. When the device is used for detecting leakage of the sodium coolant of a fast breeder, the device operates only when there has been leakage of sodium ions. The device may not operate sodium ions of an extremely low concentration, which are generally contained in the atmosphere.

Sodium ions reach the gate electrode 22 after passing through the protection layer 28. The gate electrode 22 comprises a conductive layer of a metal of relatively great thickness. Metals do not generally allow migration of sodium ions. Therefore, the gate electrode 22 does not pass sodium ions, so that the sensitivity of the device is degraded. In the device of the present invention, the metal ion introducing passage 24 extends through the gate electrode 22 in the direction of thickness thereof. The field insulating layer 26 of silicon oxide ($SiO_2$) is filled in the metal ion introducing passage 24. However, silicon oxide allows easy migration of sodium ions. Therefore, sodium ions which have passed through the protection layer 28 reach the gate oxide film 20 through the metal ion introducing passage 24. By the incorporation of the passage 24, sodium ions of sufficiently low concentration may be detected.

When the sodium ions reach the gate oxide film 20, the positive gate voltage is increased by the positive charge of sodium ions. Thus, the source current (or the drain current) increases. The source electrode is connected to the signal processing means 40. When the rate of increase of the source current exceeds a predetermined value, the signal processing means 40 produces a signal representing the presence of sodium ions in the atmosphere. Thus, the presence of sodium ions is detected.

According to the metal ion detecting device of this embodiment, the metal ion introducing passage 24 is formed only in the gate electrode 22. Therefore, the device of this embodiment may be manufactured according to the manufacturing method of a conventional MOSFET without significant modification. First, the n-type impurity regions 12 and 14, the gate oxide film 20 are formed in and on the semiconductor substrate 10.

The field insulating layer 26 is formed on the entire surface of the structure. Parts of the field insulating layer 26 where the source electrode 16, the drain electrode 18 and the gate electrode 22 are to be formed are selectively removed by photoetching. Metal layers are formed at these parts to form the source electrode 16, the drain electrode 18, and the gate electrode 22. Therefore, in the device of this embodiment, the metal ion introducing passage 24 may be formed by slightly changing the mask pattern used for photoetching of the field insulating layer 26. For this reason, the device of this embodiment may be manufactured with manufacturing equipment for conventional MOSFETs. Since the metal ion introducing passage 24 is in the form of a slit extending along the longitudinal direction of the pattern of the gate electrode 22, the mask pattern to be used in photoetching becomes simple and is easy to manufacture.

Figure 4:
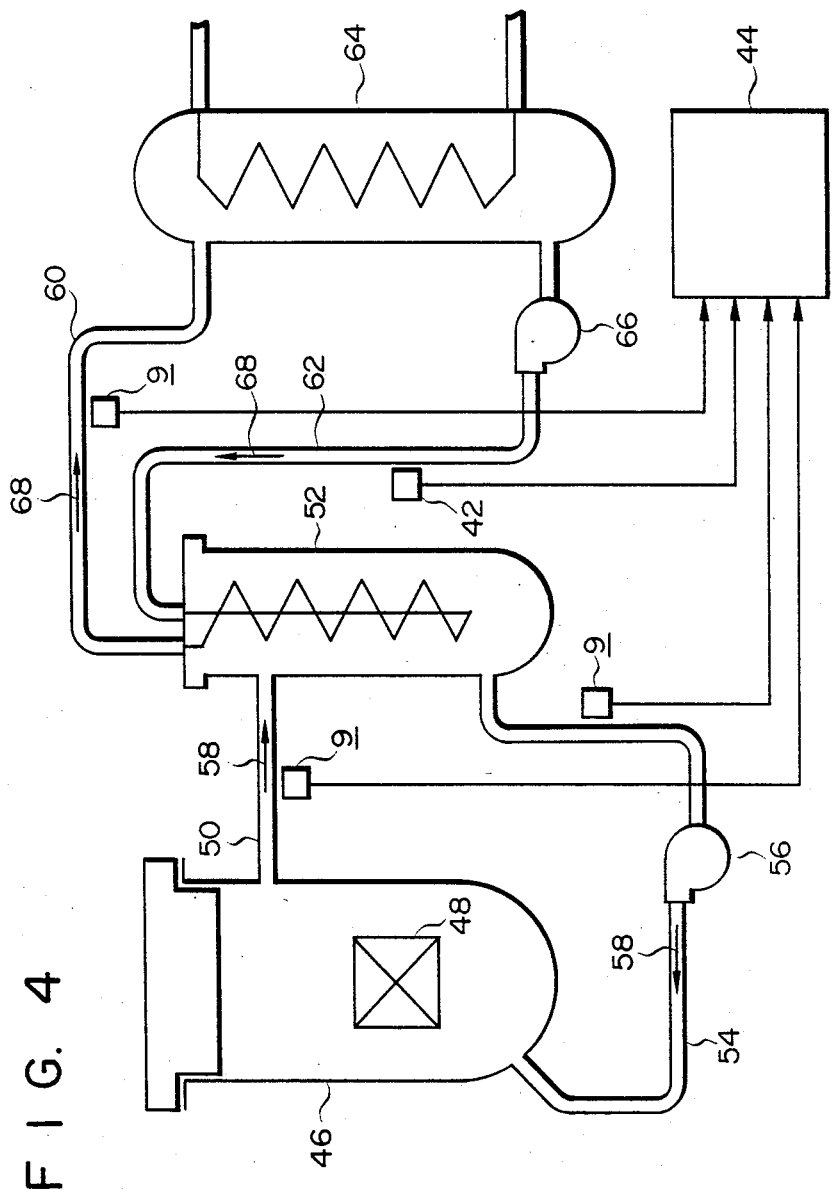
FIG. 4 is a schematic view for explaining fast breeder facilities.

The metal ion detecting device of the present invention is particularly suitable for detecting leakage of liquid sodium used as a coolant in a fast breeder. FIG. 4 shows a model of general fast breeder facilities. The facility includes a reactor vessel 46. The reactor vessel 46 houses a reactor core 48 therein. The upper part of the reactor vessel 46 is connected to the upper part of an intermediate heat exchanger 52 through a hot leg pipe 50. The lower part of the reactor vessel 46 is connected to the lower part of the intermediate heat exchanger 52 through a cold leg pipe 54. Liquid sodium as the primary coolant is let to flow through the reactor vessel 46, the hot leg pipe 50, the intermediate heat exchanger 52, and the cold leg pipe 54 by a pump 56 in the direction indicated by arrow 58. The intermediate heat exchanger 52 is connected to a steam generator 64 through a hot leg pipe 60 and a cold leg pipe 62. Liquid sodium as the secondary coolant is let to flow through the intermediate heat exchanger 52, the hot leg pipe 60, the steam generator 64 and the cold leg pipe 62 by a pump 66 in the direction indicated by arrow 68. The primary coolant which has received heat from the reactor core 48 flows to the intermediate heat exchanger 52 through the hot leg pipe 50. At the intermediate heat exchanger 52, heat of the primary coolant is transmitted to the secondary coolant. The secondary coolant which has received heat reaches the steam generator 64 through the hot leg pipe 60. Heat of the secondary coolant is thus transmitted to water and steam is generated.

A plurality of metal ion detecting elements 9 of the present invention is arranged in the vicinity of the facilities or piping through which liquid sodium flows. Output signals from the metal ion detecting elements 9 are supplied to a leakage detecting circuit 44 for detecting leakage of sodium from facilities or piping.

Figure 5:
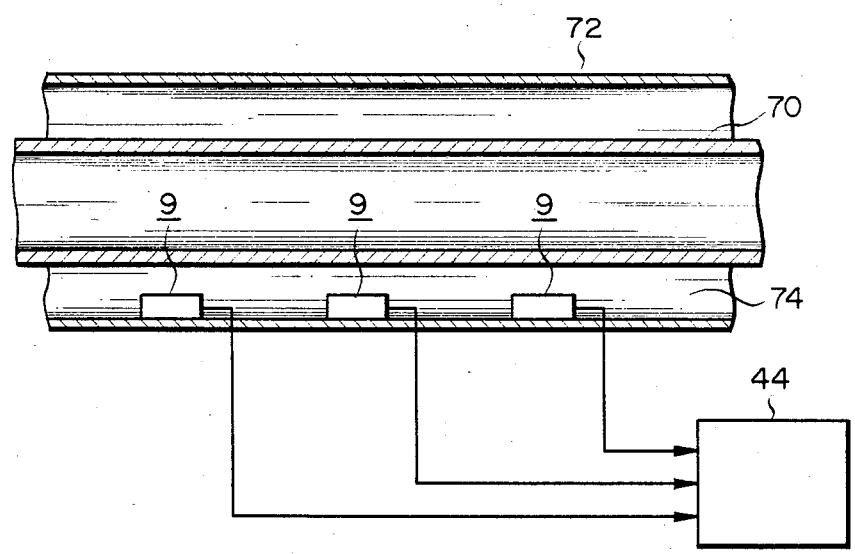
FIG. 5 is a view for explaining the arrangement of a metal ion detecting element of the device of the present invention in the vicinity of piping through which sodium flows.

The metal ion detecting elements 9 are arranged in the vicinity of the piping preferably in the manner as shown in FIG. 5. An enclosing duct 72 surrounds a pipe 70 through which sodium flows. The metal ion detecting elements 9 of the present invention are arranged in a space 74 defined by the outer surface of the pipe 70 and the inner surface of the enclosing duct 72. A gas which does not contain sodium ions and other metal ions such as argon gas is sealed in the space 74. The gas such as argon gas is sealed in the space 74 so as to prevent detection of metal ions naturaly contained in the air by the device. When argon gas is sealed in the space 74, the space 74 is kept in the atmosphere wherein the concentration of the metal ions is below a predetermined value unless sodium ions leak. Thus, if the metal ion detecting elements 9 are placed in argon gas, the device operates only when there has been leakage of sodium ions.

Figure 6:
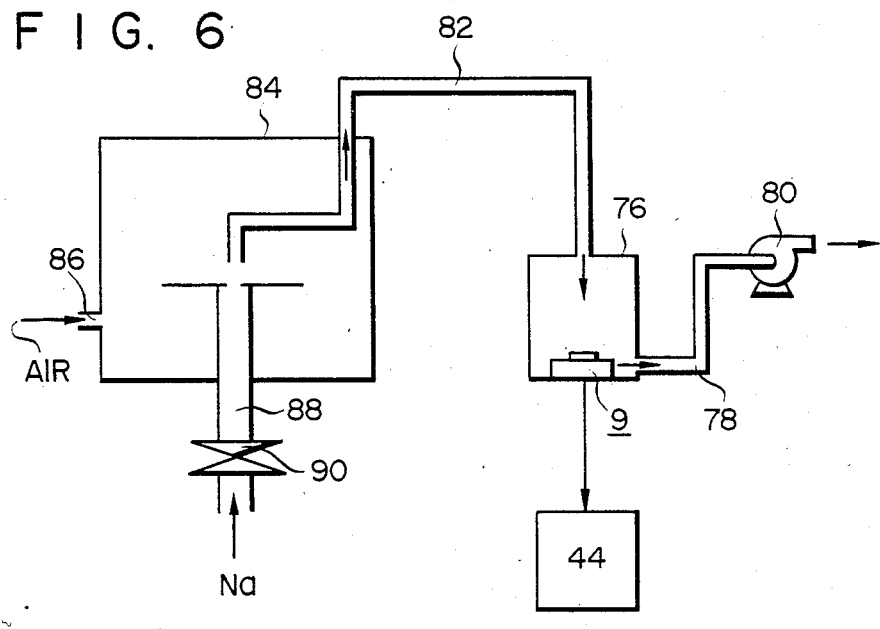
FIG. 6 is a view showing a device for sodium leakage test for the purpose of testing performance of the metal ion detecting device according to the present invention.

The sensitivity of the metal ion detecting device of the present invention was examined by the sodium leakage test with the device as shown in FIG. 6. The metal ion detecting element 9 is placed in a container 76. The bottom of the container 76 is connected to an evacuating pump 80 through an evacuating pipe 78. The container 76 communicates with a glove box 84 through a communicating pipe 82. An air inlet hole 86 for supply of air is formed in the glove box 84. A sodium inlet pipe 88 communicates with the glove box 84. A valve 90 is arranged in the sodium inlet pipe 88.

Figure 7:
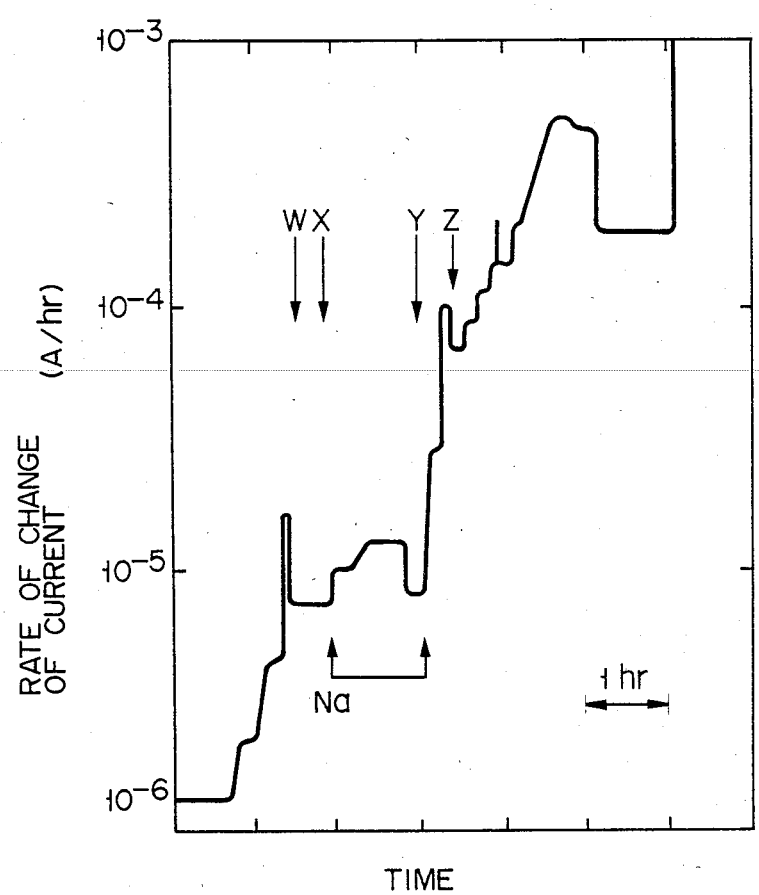

According to the test procedure, the evacuating pump 80 was operated and the valve 90 was opened. Then, air and sodium vapor flew in the direction indicated by arrows in the figure, and the air containing sodium ions reached the container 76. The metal ion detecting element 9 detected sodium ions. The test results are shown in FIG. 7. It is seen from the graph shown in FIG. 7 that when sodium reaches the container 76 (arrow Y), the source current abruptly changes and the rate of change (A/h) of the source current increases to ten times its original value.

Figure 8:
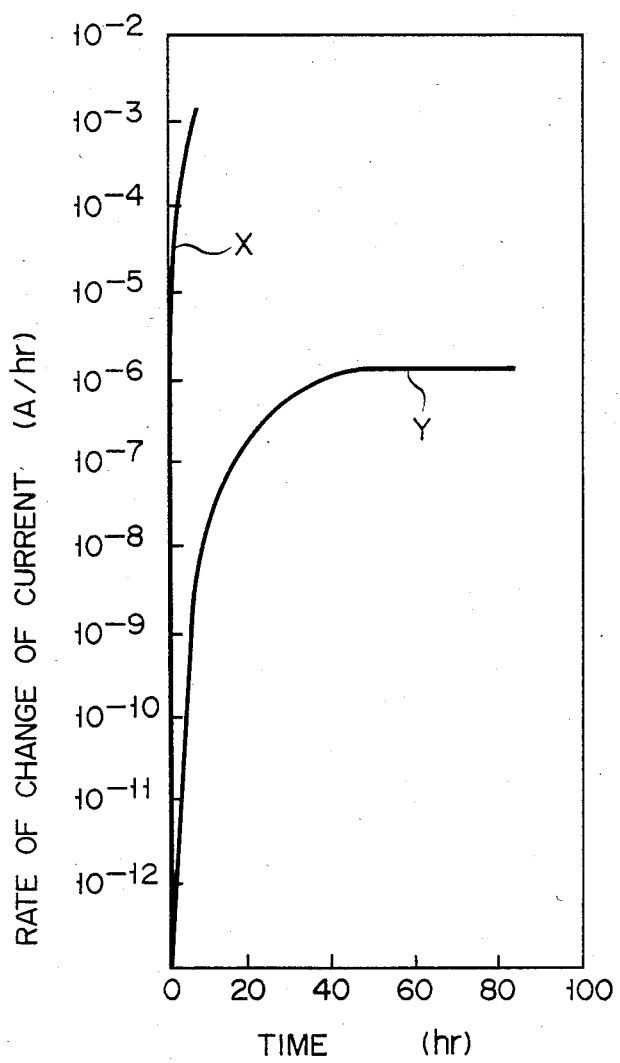

Curve X in FIG. 8 shows the same result as in FIG. 7 by elongating the abscissa. Curve Y in FIG. 8 represents the rate of change of the source current when the metal ion detecting element 9 is placed in a control chamber.

The protection layer 28 of the ion detecting device used in this test is made of P.S.G., and had a thickness of 1.25±0.25 $\mu$m. The gate voltage was 16 V, and the source-drain voltage was 200 mV.

Figure 9:
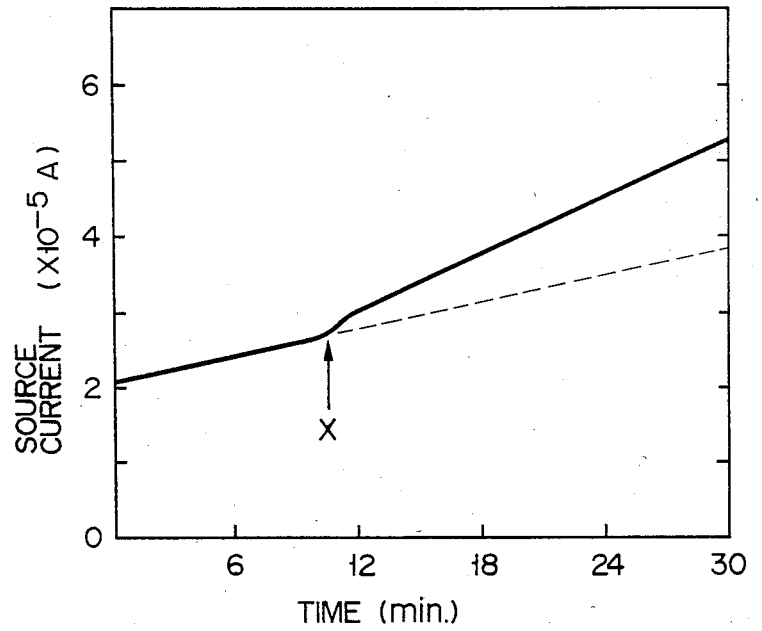
FIGS. 7 to 9 and 11 are views showing results of performance test of the device of the present invention.

Another test was performed using the same testing apparatus. The evacuating pump 80 was operated with the valve 90 kept closed. After 10 minutes, the valve 90 was opened, and sodium vapor was introduced. The obtained result is shown in FIG. 9. The valve 90 was opened at a time corresponding to X. It is seen from the graph that the source current increases when the valve 90 is opened. The increase in the source current before introduction of sodium ions is attributed to sodium ions naturally contained in the air (the experiment was performed at a location near the coast and the air contained a considerable amount of sodium ions). Therefore, when sodium leakage of a fast breeder is to be detected with the device of the present invention, the device is preferably placed in an argon atmosphere.

Using the same testing apparatus, changes in the source current of the metal ion detecting device in an argon atmosphere and in air were examined. In this test, the valve 90 was kept closed. Therefore, sodium ions were not introduced. First, argon gas (99.99% purity) was introduced into the glove box 84 through the air inlet hole 86. After 5 minutes, introduction of the argon gas was stopped and air was supplied instead.

Figure 10:
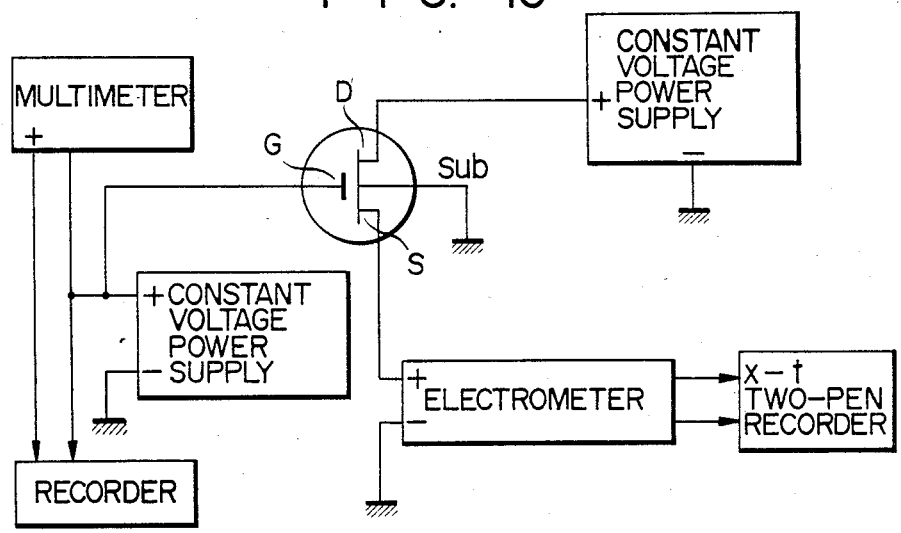
FIG. 10 is a block diagram of a device used in a performance test of the device of the present invention.

The circuit used in this test is shown in FIG. 10. The source-drain voltage was 200 mV. The gate voltage was set at an optimal value while measuring the source current. Three metal ion detecting elements formed on a single semiconductor substrate were used in this test. The protection layer 28 is made of phosphor silicate and had a thickness of 0.3 or 1.2 $\mu$m.

Figure 11:
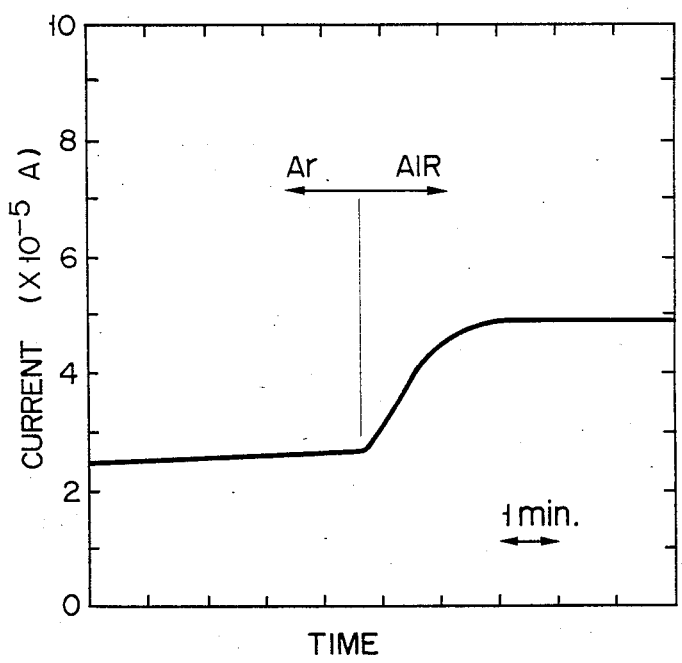

The test results are shown in FIG. 11. It is seen from this graph that the source current abruptly increases when the atmosphere is switched from argon gas to air.

Thus, the device of the present invention is capable of detecting sodium ions of a concentration as low as that naturally contained in the air and is excellent in sensitivity.

The present invention is not limited to the particular embodiment described above. For example, the metal ion introducing passage is not limited to a slit but may be a number of through holes. The only requirement is that a metal ion introducing passage be formed in the gate electrode in the direction of its thickness.

An n-type semiconductor substrate may be used. In this case, p-type impurity regions are formed as source and drain regions. In this case, a negative voltage is applied to the gate electrode. When sodium ions are introduced to the gate oxide layer, the source current decreases.

What we claim is:

1. A device for detecting metal ions comprising:
   (a) a metal ion detecting element, including
   a semiconductor substrate of first conductivity type,
   a source region of second conductivity type opposite to the first conductivity type, formed in said semiconductor substrate,
   a source electrode formed on said source region,
   a drain region of second conductivity type formed in said semiconductor substrate,
   a drain electrode formed on said drain region,
   a gate oxide film formed on the surface of said semiconductor substrate between said source region and said drain region,
   a gate electrode formed on said gate oxide film, and
   a metal ion introducing passage formed in said gate electrode in the direction of thickness thereof so as to allow the metal ions to be detected to migrate to said gate oxide film,
   wherein said gate electrode is a conductive layer formed on the surface of said gate oxide film and said metal ion introducing passage is formed in said conductive layer all through the thickness thereof;
   (b) a means, connected to said metal ion detecting element, for making a current flow between said source region and said drain region;
   (c) a means, connected to said metal ion detecting element, for detecting a change of the strength of the current flowing through said metal ion detecting element, said change being brought by the electric charge of metal ions which reached said gate oxide film;
   (d) an insulating layer formed in said metal ion introducing passage; and
   (e) a protection layer for preventing gate oxide film from being easily imbued with metal ions, which covers said metal ion introducing passage and which is made of a material which does not allow easy migration of the metal ions therethrough.

2. The device according to claim 1, wherein said conductive layer is made of a metal.

3. The device according to claim 1, wherein said conductive layer is formed in a meandering manner on said semiconductor substrate, and said metal ion introducing passage is formed in a form of a slit extending along said conductive layer.

4. The device according to claim 1, wherein said insulating layer is a field insulating layer formed on the entire surface of said semiconductor substrate.

5. The device according to claim 1, wherein said field insulating layer is made of silicon dioxide.

6. The device according to claim 1, wherein said protection layer is made of a member selected from the group consisting of phosphor silicate glass, silicon nitride, and aluminum oxide.

7. The device according to claim 6, wherein said protection layer has a thickness of 0.3 to 1.2 $\mu$m.

8. The device according to claim 1, further comprising:
   means for applying a positive voltage to the gate electrode.

* * * * *